US010918704B2

(12) United States Patent
Bartůňková et al.

(10) Patent No.: US 10,918,704 B2
(45) Date of Patent: *Feb. 16, 2021

(54) MEANS AND METHODS FOR ACTIVE CELLULAR IMMUNOTHERAPY OF CANCER BY USING TUMOR CELLS KILLED BY HIGH HYDROSTATIC PRESSURE AND DENDRITIC CELLS

(71) Applicant: SOTIO a.s., Prague (CZ)

(72) Inventors: Jiřina Bartůňková, Prague (CZ); Radek Špíšek, Prague (CZ)

(73) Assignee: SOTIO a.s., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/365,027

(22) Filed: Mar. 26, 2019

(65) Prior Publication Data
US 2019/0216909 A1    Jul. 18, 2019

Related U.S. Application Data

(62) Division of application No. 13/541,703, filed on Jul. 4, 2012, now abandoned.

(60) Provisional application No. 61/504,387, filed on Jul. 5, 2011.

(51) Int. Cl.
*C12N 5/00* (2006.01)
*C12N 5/02* (2006.01)
*A61K 39/00* (2006.01)

(52) U.S. Cl.
CPC .. *A61K 39/0011* (2013.01); *A61K 2039/5152* (2013.01); *A61K 2039/5154* (2013.01); *A61K 2039/572* (2013.01); *A61K 2039/80* (2018.08)

(58) Field of Classification Search
None
See application file for complete search history.

(56) References Cited

U.S. PATENT DOCUMENTS

2002/0146396 A1    10/2002    Albert et al.
2008/0286314 A1    11/2008    Palucka et al.
2014/0086957 A1    3/2014    Bartunkova et al.

FOREIGN PATENT DOCUMENTS

WO    WO 2006/095330    9/2006

OTHER PUBLICATIONS

Luigi Buonaguro, et al., "Translating Tumor Antigens into Cancer Vaccines" Clinical and Vaccine Immunology, Jan. 2011, vol. 18, No. 1; p. 23-34.
Kristina Subik, et al., "The Expression Patterns of ER, PR, HER2, CK5/6, EGFR, Ki-67 and AR by Immunohistochemical Analysis in Breast Cancer Cell Lines" Breast Cancer: Basic and Clinical Research 2010:4; pp. 35-41.
Wanyi Tai, et al., "The role of HER2 in cancer therapy and targeted drug delivery" J Control Release. Sep. 15, 2010; 146(3): 264-275; pp. 1-28.
Frank et al. "Harnessing Naturally Occurring Tumor Immunity; A Clinical Vaccine Trial in Prostate Cancer", PLOS ONE, vol. 5, No. 9, Jan. 1, 2010, p. E12367.
Minarik et al. "Phase I/II of Clinical Study of Prostate Cancer Immunotherapy Using Dendritic Cell Vaccination Strategy First Results", European Urology Supplements, vol. 9, No. 6, Sep. 1, 2010, p. 629.
Weiss et al. "Ex vivo- and in vivo-induced dead tumor cells as modulators of antitumor responses", Annals of the New York Academy of Sciences, vol. 1209, No. 1, Oct. 1, 2010, pp. 109-117.
Weiss et al. "High hydrostatic pressure treatment generates inactivated mammalian tumor cells with immunogeneic features", Journal of Immunotoxicology, vol. 7, No. 3, Sep. 1, 2010, pp. 194-204.
Kroemer, Guido et al., Annual Review of Immunology, Mar. 2013, vol. 31: 51-72.
Diehl, Peter et al., Oncology Reports, Mar. 2003, vol. 10: 1851-55.
Richert et al., 1986, Canc. Immunol., Immunother, vol. 22: 119-124.
Sawai et al., 2011, Biochem. Biophys. Res. Comm. vol. 411: 569-73.
Korn et al., 2004, Cell. Mol. Biol. vol. 50: 469-77.
Fucikova et al., 2014, Int. J. cancer, pp. 1-13.
Hingorani, R et al., Aug. 2011, BD Biosciences.
Shortman, K. et al., Nat Rev Immunol, Mar. 2002, vol. 2: 151-161.
Casares et al., 2005, J. Exp. Med. vol. 202: 1691-1701.
Benjamin Frey, et al., Cells Under Pressure—Treatment of Eukaryotic Cells with High Hydrostatic Pressure, from Physiologic Aspects to Pressure Induced Cell Death, Current Medicinal Chemistry, 2008, 15, pp. 2329-2336.
Turnis, ME & Rooney, CM, "Enhancement of dendritic cells as vaccines for cancer," Immunotherapy, Nov. 2010, 2(6): 847-862.
Banerjee, et al., "Expansion of FOXP3high regulatory T cells by human dendritic cells (DCs) in vitro and after injection of cytokine-matured DCs in myeloma patients," *Blood* 108, 2655-2661, (2006).
Cannon, M. J. & O'Brien, T. J., "Cellular immunotherapy for ovarian cancer," *Expert Opin Biol Ther* 9, 677-688, (2009).
Curiel, T. J. "Tregs and rethinking cancer immunotherapy," *J Clin Invest* 117, 1167-1174, (2007).
Dhodapkar, M. V., Dhodapkar, K. M. & Palucka, A. K. "Interactions of tumor cells with dendritic cells: balancing immunity and tolerance," *Cell Death Differ* 15, 39-50, (2008).
Han, S. et al. "Overcoming immune tolerance against multiple myeloma with lentiviral calnexin-engineered dendritic cells" *Mol Ther* 16, 269-279, (2008).
Naumann, K., et al., "Activation of Dendritic Cells by the Novel Toll-Like Receptor 3 Agonist RGC100," Clinical and Developmental Immunology, vol. 2013, Article ID 283649, 2013.
Pharmaceutical Technology Editors, "Removing Endotoxin from biopharmaceutical solutions," Pharmaceutical Technology Europe, vol. 21, Issue 10, Oct. 1, 2009.

(Continued)

Primary Examiner — Amy E Juedes
(74) Attorney, Agent, or Firm — Kagan Binder, PLLC

(57) ABSTRACT

Disclosed are pharmaceutical compositions for inducing an immune response against tumor cells comprising tumor cells which are made apoptotic by treatment with high hydrostatic pressure and dendritic cells, and methods for producing such compositions.

22 Claims, 11 Drawing Sheets

(56) References Cited

OTHER PUBLICATIONS

Hradilova, Nada, et al. "Generation of dendritic cell-based vaccine using high hydrostatic pressure for non-small cell lung cancer immunotherapy." *PloS one* 12.2 (2017): e0171539.
"Public summary of opinion on orphan designation: Autologous dendritic cells pulsed with killed ovarian cancer cells and matured by TLR3 ligand ex vivo for the treatment of ovarian cancer," European Medicines Agency, May 15, 2018.
Sotio Press Release, "Sotio Receives Positive Opinion for Orphan Drug Designation for DCVAC/OvCa from European Medicines Agency (EMA)," Prague, Mar. 28, 2018.
Adams et al., 2003, Vaccine vol. 21: 787-790.
Spisek et al., 2007, Blood vol. 109: 4839-4845.
Demaria et al., 2005, J. Leuk. Biol. vol. 77: 361-368.

Design of cancer immunotherapy

Expression of immunogenic cell death markers after HHP treatment

Expression of immunogenic cell death markers after HHP treatment

HHP treatment enhances phagocytosis of dead tumor cells by DCs

Interaction with HHP killed tumor cells induces expression of activation markers on dendritic cells Combination of HHP killed tumor cells and dendritic cells induces prostate and ovarian cancer cells specific immune response

MEANS AND METHODS FOR ACTIVE CELLULAR IMMUNOTHERAPY OF CANCER BY USING TUMOR CELLS KILLED BY HIGH HYDROSTATIC PRESSURE AND DENDRITIC CELLS

CROSS-REFERENCE TO RELATED PATENT APPLICATIONS

This application is a Divisional of U.S. application Ser. No. 13/541,703, filed Jul. 4, 2012 and claims the benefit of priority under 35 U.S.C. Section 119(e) of U.S. Application Serial No. 61/504,387, filed Jul. 5, 2011, which are hereby incorporated by reference in their respective entireties.

BACKGROUND OF THE PRESENT INVENTION

Diseases caused by different tumors are still major problems in medicine and human health. The combination of surgery, chemotherapy and radiotherapy greatly improved the prognosis of cancer patients. Despite that this approach results frequently in a significant reduction of tumor mass, a small population of precursor tumor cells or cancer stem cells often survives and subsequently gives rise to a new population of tumor cells that leads to a relapse. Even if the main tumor is removed by surgical and/or other treatments minor amounts of circulating tumor cells may cause metastatic tumors in different areas of the body. Therefore, there exists a permanent need for alternative medicaments and methods of treatment which may be used alone or preferably be combined with other methods of tumor treatment.

PRIOR ART

WO 2006/095330 describes methods for inhibiting growth of cell populations by thermally, mechanically and/or chemically damaging antigen-bearing cells and introducing said cells as aggregate with antigen-presenting cells into patients.

Frank et al. "Harnessing Naturally Occurring Tumor Immunity; A Clinical Vaccine Trial in Prostate Cancer", PLOS ONE, vol. 5, no. 9, 1 Jan. 2010 (2010-01-01), page E12367, disclose a tumor vaccine comprising autologous dendritic cells and apoptotic UV-irradiated LNCaP cells.

Minarik et al. "Phase I/II of Clinical Study of Prostate Cancer Immunotherapy Using Dendritic Cell Vaccination Strategy—First Results", European Urology Supplements, vol. 9, no. 6, 1 Sep. 2010, page 629, disclose the preliminary results of a phase I/II clinical study of prostate cancer immunotherapy using dendritic cells pulsed with apoptotic LNCaP cells killed by UVA irradiation.

Weiss et al. "Ex vivo- and in vivo-induced dead tumor cells as modulators of antitumor responses", Annals of the New York Academy of Sciences, vol. 1209, no. 1, 1 Oct. 2010 (2010-10-01), pages 109-117, disclose high hydrostatic pressure treatment of tumor cells. The dead tumor cells are directly used as cancer vaccines in animal models.

Weiss et al. "High hydrostatic pressure treatment generates inactivated mammalian tumor cells with immunogeneic features", Journal of Immunotoxicology, vol. 7, no. 3, 1 Sep. 2010, pages 194-204, disclose that high hydrostatic pressure treatment induces apoptosis wherein tumor cells are inactive and immunogenic. Antibodies directed against tumor cells have been produced and identified in a mouse model.

US 2008/0286314 discloses cancer vaccines comprising antigen presenting cells loaded with heat-shocked cancer cells which are non-apoptotic which can be used for treating cancer patients.

SUMMARY OF THE PRESENT INVENTION

The present invention relates to pharmaceutical compositions which can be used for the induction of anti-tumor immune response, in particular in tumor vaccination causing the body to produce an immunogenic reaction against tumor cells.

Tumor cells killed by standard modalities such as irradiation are normally non-immunogenic. If used for the generation of cancer immunotherapy products, irradiated tumor cells need to be administered in combination with a potent adjuvant. When used for pulsing of antigen presenting cells, such as dendritic cells, irradiated killed tumor cells do not provide an activating signal. Dendritic cells thus need to be activated by another substance, such as pathogen derived molecules.

A novel process is disclosed that induces an immunogenic death of human tumor cells, in particular ovarian and prostate cancer cells and acute lymphoblastic leukemia cells of human origin. Tumor cells killed by high hydrostatic pressure (in the following also: HHP) provide a potent activation stimulus to dendritic cells, in particular to immature dendritic cells, even in the absence of additional stimuli. Tumor cells killed by this method express high levels of immunogenic cell death markers and dendritic cells loaded with those immunogenic tumor cells induce high numbers of tumor specific T lymphocytes without expanding undesirable regulatory T lymphocytes. The experimental data of the present invention show that the combination of tumor cells killed by the application of high hydrostatic pressure and dendritic cells results in the phagocytosis and efficient presentation of tumor antigens and in the induction of strong anti-tumor immune responses.

Tumor cells are not or only weakly immunogenic and they usually do not have the capacity to induce a tumor specific immune response if used in the absence of a powerful adjuvant. Recent studies have shown that tumor cells killed by some chemotherapeutics, such as bortezomib, oxaliplatin and anthracyclines, can induce a tumor-specific immune response. This immunogenic cell death is characterized by molecular events shared for all described chemotherapeutics. Within hours after the initiation of immunogenic cell death, preapoptotic tumor cells translocate calreticulin and heat shock proteins from the endoplasmic reticulum to the cell surface together with other molecules that serve as 'eat me' signals (phosphatidylserine).

At the same time, tumor cells undergoing immunogenic tumor cell death downregulate the expression of 'don't eat me' signals (such as surface CD47) to facilitate tumor-cell recognition and engulfment by dendritic cells. Additionally, following permeabilization of the plasma membrane, cells release the late apoptosis marker high mobility group box 1 (HMGB1) into the extracellular milieu. HMGB1 can bind several pattern recognition receptors (PRRs), such as Toll-like receptor 2 (TLR2), TLR4 and receptor for advanced glycosylation end products (RAGE). The release of this protein seems to be required for optimal presentation of antigens from dying tumor cells, T-cell priming by dendritic cells and subsequent T-cell-mediated elimination of the tumor.

Use of tumor cells killed in such a way that they become immunogenic is extremely important for the design of cancer immunotherapeutic strategies. Administration of immunogenic tumor cells can induce a tumor specific immune response that will then control the growth of tumor cells. This will slow down or even stabilize the progression of the disease and improve the prognosis of cancer patients. It is also assumed that the distribution of tumor cells circulating in the body and the formation of metastases can be at least substantially reduced.

PREFERRED EMBODIMENTS OF THE PRESENT INVENTION

A novel method and pharmaceutical compositions are disclosed that induce an immunogenic cell death of human tumors, in particular ovarian and prostate cancer cells and acute lymphoblastic leukemia cells to a much higher extent than recently described chemotherapeutics. Tumor cells killed by this method and captured by dendritic cells express high levels of immunogenic cell death markers and induce high numbers of tumor specific T lymphocytes without inducing regulatory T cells that could inhibit anti-tumor immune response. It has been found that the degree of the anti-tumor immune response obtained by the combination of tumor cells treated according to the present invention and dendritic cells is about 10-fold higher than the immune response induced by immunogenic tumor cells alone.

The general principle of a preferred cancer immunotherapy protocol based on the administration of mature dendritic cells (DCs) loaded with killed tumor cells is shown in FIG. 1. All steps of the generation of the final pharmaceutical composition are performed under Good Manufacturing Practice conditions in GMP facility.

In a preferred embodiment the first step in the process of generation of the pharmaceutical composition for each patient is a leukapheresis performed for the purpose of collecting large numbers of monocytes from the peripheral blood. In a preferred embodiment the leukapheretic product is then diluted in a suitable buffer, such as PBS+1 mM EDTA (Lonza, Vierviers, Belgium) and mononuclear cells are separated by Premium Ficoll Paque (GE Healthcare, Little Chalfont, UK) gradient centrifugation. Collected mononuclear cells (PBMC) are then washed [e.g. in PBS+1 mM EDTA (Lonza)], resuspended in Cell Gro medium and plated in triple flasks (e.g. NUNC, Roskilde, Denmark) at $1\times10^6$ cells per $cm^2$ of surface area. After two hours non-adherent cells are washed with PBS (Lonza). Adherent monocytes are cultured for 6 days in Cell Gro medium with 20 ng/ml of IL-4 (Gentaur) and 500 U/ml of GM-CSF (Gentaur), fresh cytokines are added on day 3.

Immature DCs are harvested on day 6 and loaded with killed tumor cells (e.g. prostate cancer cell line, ovarian cancer cell line, acute lymphoblastic leukemia cell line). Freshly thawed, immature DCs (day 3-6) are fed with tumor cells at a fixed DC: tumor cell ratio of 5:1 for 4 h. The ratio of dendritic cells to treated tumor cells is preferably within a range between 1:1 up to 10:1, more preferred between about 4:1 and 6:1.

According to the present invention dendritic cells which are in various stages of differentiation, maturation and/or activation can be used. The maturation stage of the dendritic cells can be influenced by maturation factors.

Tumor cell-pulsed DCs are then preferably matured by 25 μg/ml of Poly I:C during overnight incubation and cryopreserved and stored in liquid nitrogen. Before administration, $1\times10^7$ mature DCs pulsed with tumor cells are resuspended in 0.9% NaCl (Baxter) and injected subcutaneously in the inguinal and brachial area within 12 hours preferably from 30 minutes up to 12 hours. Administration of this form of cancer immunotherapy is preferably repeated in regular intervals of 2-6 weeks in order to continuously boost the immune response. It is assumed that the method disclosed herein prevents the reestablishment of tumor-induced immune tolerance. The therapeutic efficacy of this form of immunotherapy has been documented in patients with prostate cancer in distinct clinical stages, biochemical relapse of the prostate cancer and castration resistant metastatic prostate cancer, presumably also in metastatic hormone-sensitive stage.

The above-described preferred embodiment is, however, in no way limiting. In the broadest scope the invention can be performed in alternative ways depending on the specific needs of tumor treatment. The above-identified preferred embodiment describes the invention whereby the tumor cells are either obtained from the patient to be treated or from tumor cell lines or tumor cell line banks. Dendritic cells are preferably also obtained from the patient to be treated.

In a more general way, however, the present invention relates to a pharmaceutical composition for inducing an immune response against tumor cells comprising
   a) tumor cells which are apoptotic, whereby apoptosis is caused by treatment with hydrostatic pressure and
   b) dendritic cells.

It is an important aspect of the present invention that the tumor cells which are used in the pharmaceutical composition are apoptotic cells and not necrotic cells. The person skilled in the art is aware of the differences between apoptosis versus necrosis. Cell death and subsequent post-mortem changes, called necrosis, are integral parts of normal development and maturation cycle. Despite the importance of this process the mechanism underlying cell death are still poorly understood although there are several publications relating to the mechanisms which occur when a cell is dying. Apoptosis in the sense of the present invention is understood as a programmed, managed form of cell death whereby necrosis is an unordered and accidental form of cellular dying.

In the present invention apoptosis is understood as a mode of cell death that occurs under normal physiological conditions and the cell is an active participant of its own demise. Cells undergoing apoptosis show characteristic morphological and biochemical features. These features include chromatine aggregation, nuclear and cytoplasmatic condensation, partition of cytoplasm and nucleus into membrane-bound vesicles (apoptotic bodies) which contain ribosomes, morphologically intact mitochondria and nuclear material. Since these apoptotic bodies are in vivo normally recognized and phagocytized by either macrophages or adjacent epithelial cells it is important that the tumor cells used in the present method resemble as close as possible apoptotic tumor cells. Apoptosis is usually limited to individual cells and does not cause inflammatory responses.

Necrosis on the other hand occurs when cells are exposed to extreme physiological conditions which may result in damage to the plasma membrane. Necrosis begins with an impairment of the cells' ability to maintain hemostasis, leading to an influx of water and extracellular ions. Intracellular organelles, most notably the mitochondria and the entire cell swells and ruptures. Due to the ultimate breakdown of the plasma membrane the cytoplasmic contents, including lysosomal enzymes, are released into the extracellular fluid. Therefore, in vivo necrotic cell death is often associated with extensive tissue damages resulting in an intense inflammatory response. It is important that the tumor cells used in the pharmaceutical compositions are apoptotic and not necrotic.

According to the present invention the apoptotic cells are produced by a treatment with high hydrostatic pressure. A high hydrostatic pressure as understood in the present invention is defined as a pressure head equal to or greater than 100 Mpa [1 MPa=10 bar=9.86923 atm=145.0377 psi]. High hydrostatic pressure can be produced by an equipment which is for example described in Weiss et al., Journal of Immunotoxicology, 2010, pp 194-209, in particular in FIG. 1.

The high hydrostatic pressure treatment of the tumor cells is preferably performed in a pressure autoclave. The tumor cells are placed in suitable cryogenic vials which are filled completely with cell suspension and closed tightly whereby the appearance of air bubbles has to be avoided. Afterwards the vials are sealed with a flexible film (e.g. parafilm®) and the prepared vials are placed in the pressure chamber which is filled with a pressure transmitting medium. Afterwards the high pressure is produced by a suitable device and the cells are maintained for a sufficient time under such high pressure.

In a preferred embodiment the hydrostatic high pressure is maintained for at least 10 minutes at a pressure of at least 200 MPa. In a more preferred embodiment the tumor cells are maintained for a time range of 10 minutes to 12 hours, preferably 10 minutes to 1 hour and especially preferred 10 to 30 minutes at a pressure in the range of 200-300 MPa, preferably 200-250 MPa.

The tumor cells to be used in the pharmaceutical composition can be derived from different sources. In one particular embodiment the tumor cells are derived from a primary tumor or from a metastatic tumor of the patient to be treated. The tumor cells can be obtained by biopsy or surgery. The tissue is disintegrated and the separated and purified tumor cells can be used immediately. It is also preferred to establish a cell line of the primary tumor and to use the so obtained cells for tumor vaccination. Alternatively the tumor cells may be obtained from suitable tumor cell lines. Such tumor cell lines may be prepared from the autologous tumor. Alternatively, tumor cells may be used which are commercially available from depository institutions such as for example ATCC.

The other component of the pharmaceutical composition are dendritic cells. According to the present invention dendritic cells in various stages can be used. It is possible to use either dendritic cells directly obtainable from the patient by separating the dendritic cells from the blood. It is, however, also possible to further classify the dendritic cells depending on their stage. In one embodiment of the present invention immature dendritic cells differentiated from the peripheral blood monocytes are used for the preparation of the tumor vaccine. It is known that there are three main types of antigen-presenting cells in the peripheral lymphoid organs that can activate T cells, namely dendritic cells, macrophages and B cells.

The most potent of these are dendritic cells whose known function is to present foreign antigens to T cells. Immature dendritic cells are located in tissues throughout the body, including the skin, gut and respiratory tract. Dendritic cells exist in two functionally and phenotypically distinct stages, immature and mature dendritic cells. Immature dendritic cells have high endocytic activity, are specialized in antigen capture and processing and reside in peripheral tissues in vivo. Immature dendritic cells play a crucial role in the induction and maintenance of peripheral tolerance. Upon exposure to pathogen-derived products or innate pro-inflammatory signals, dendritic cells lose their phagocytic activity and migrate to draining lymph nodes while becoming mature dendritic cells. Mature dendritic cells have a high antigen-presenting capability and T-cell stimulatory capacity due to the expression of high levels of antigen-presenting, adhesion and co-stimulatory molecules as well as other dendritic cell-specific markers such as CD83 and DC-LAMP.

The immature dendritic cells to be used in the pharmaceutical composition may be obtained from different sources. In a preferred embodiment the immature dendritic cells are differentiated from the monocytes of the patient to be treated. Alternatively, however, the immature dendritic cells may be obtained from other sources such as commercially available blood products obtainable from blood collecting agencies.

For the preparation of a pharmaceutical composition according to the present invention suitable immature dendritic cells are prepared. Dendritic cells (DCs) can be prepared by different methods and may exhibit different properties. In a preferred embodiment of the present invention dendritic cells are obtained from monocytes isolated by leukapheresis.

DCs comprise less than 1% of mononuclear cells in the peripheral blood. Leukapheresis can be used to isolate approximately $10^6$ to $10^7$ dendritic cells and may be combined with positive or negative selection techniques. While the direct isolation of dendritic cells from peripheral blood allows rapid preparation of dendritic cells it may require repeated leukapheresis if multiple immunizations are required in a protocol.

In a preferred embodiment of the present invention monocytes are enriched from leukapheresis by adherence on plastic material. The dendritic cells are differentiated in the presence of cytokines, preferably a cocktail of various cytokines, whereby a granulocyte macrophage-colony stimulating factor (GM-CSF) combined with interleukin 4 is preferred.

A particularly preferred method of preparing dendritic cells is to generate them ex vivo. Monocytes are dendritic cell precursors which may be enriched from peripheral blood mononuclear cells by techniques such as leukapheresis, plastic adherence, density gradient centrifugation, positive selection of CD14+ cells, negative selection of B- and T-cells and combinations thereof. DC may be cultivated and differentiated by treating an enriched precursor cell population for approximately 3-7, preferably 7 days with cytokines, in particular with granulocyte macrophage-colony stimulating factor (GM-CSF)+interleukin 4 or interleukin 13. An advantage of this embodiment is that more than $10^9$ DC may be prepared from a single leukapheresis product and such a preparation may be used for multiple further vaccinations by cryopreserving the DCs preparation preferably in liquid nitrogen. While DCs may be cultured in a variety of media it is preferred to use either serum-free media or media containing autologous serum. For the industrial preparation of the pharmaceutical composition it is particularly preferred to prepare the immature dendritic cells in a large scale in such a manner that the occurrence of anaphylactic reactions (e.g. due to fetal calf serum) or the contamination of viruses is avoided.

In the next step of the preparation of the pharmaceutical composition the immature dendritic cells are loaded with the apoptotic tumor cells which are obtained by treatment with high hydrostatic pressure. In a preferred embodiment the immature dendritic cells which were brought into contact with the apoptotic tumor cells are matured by using a variety of stimuli such as the addition of Tumor Necrosis Factor a (TNF-α) or lipopolysaccharide or poly I:C.

The obtained pharmaceutical composition can be preserved for the administration, preferably by cryopreservation. The cryopreservation of biospecimen is widely practiced in clinical medicine and biomedical research. However, the impact of this process on cell viability and particularly function sometimes may be underestimated. Therefore, the used method of freezing of the cell preparation prior to use in cancer vaccine should be viewed with caution. The effect of cryopreservation certainly depends on the specific cells used and it has to be examined whether the biological activity of the pharmaceutical composition is altered by the cryopreservation. It may be required to add protective components like non-immunogenic polysaccharides or DMSO.

The pharmaceutical composition of the present invention can be administered intravenously (IV), intradermally, subcutaneously or intralymphatically whereby subcutaneously is particularly preferred.

The optimal dose and frequency of immunization of the pharmaceutical composition depends on the type of tumor, the age and condition of the patient and the stage of progression of the tumor disease. In a preferred embodiment there is first applied an immunizing dose of the pharmaceutical composition which can be followed by long-term administration of booster injections applied in intervals ranging from 2 to 8 weeks.

The tumor vaccination as described herein can be applied to all forms of tumors successfully. In preferred embodiments the pharmaceutical compositions are for use in the treatment of cancer patients which are in a late stage of cancer, but also in the early stage of cancer. In an especially preferred embodiment the tumor vaccination is applied to patients at a late stage of prostate cancer with hormone treatment resistant metastatic prostate cancer. Under "early stage of cancer" such forms of cancer are understood wherein diagnosis is possible. Frequently the patients do not show signs of the disease. In "late stages of cancer" the patient suffers frequently from severe consequences of the disease like pain or weakness.

Although it is known in the art to use adjuvant agents in tumor therapy vaccination it is preferred in the course of the present invention not to use any further adjuvant such as lipopolysaccharide, incomplete Freund's adjuvant or heat shock proteins.

It is an important aspect of the present invention that the tumor cells treated with high hydrostatic pressure are in such a stage that they cannot grow and form a metastatic tumor after application to the patient. This has been proven by number of experimental approaches, including the clonogenic assays.

The pharmaceutical composition as described herein can be used for the treatment of a human by cancer immunotherapy (vaccination). The tumor cells which can be derived from a patient to be treated are brought to an apoptotic stage with the high hydrostatic pressure treatment described above. Alternatively suitable tumor cell lines are used. Immature dendritic cells are obtained preferably by leukapheresis from the same patient and the cells are cultured ex vivo by treatment with cytokines. A suitable amount of such immature dendritic cells (e.g. $10^7$-$10^8$ cells) is loaded with the apoptotic tumor cells whereby the optimal range of immature dendritic cells : apoptotic tumor cells is 10:1 to 1:1, preferably 5:1 to 3:1.

After maturation of the dendritic cells the pharmaceutical composition can be applied to the patient. Dendritic cells which have captured tumor cells killed by high hydrostatic pressure can be used directly for tumor vaccination. It is, however, possible to further activate or mature the cells, for example by treatment with cytokines before administration to the patient.

According to the present invention the following materials and methods are preferably used:

It has been shown that a treatment of ovarian and prostate cancer cells and acute lymphoblastic leukemia cells by 10 min with high hydrostatic pressure (200 MPa) at about 21° C. leads to the induction of an immunogenic cell death of tumor cells. Tumor cells killed by HHP (high hydrostatic pressure) are immunogenic to much higher extent than tumor cells killed by anthracyclines, the only cytostatics known to induce immunogenic cell death., or by UV-irradiation. HHP-killed immunogenic tumor cells are avidly phagocytosed by antigen presenting cells and induce their maturation even in the absence of additional pathogen-derived stimuli, such as LPS. Antigen presenting cells loaded with HHP killed tumor cells induce a robust CD4 and CD8 mediated tumor specific T cell responses and do not induce potentially harmful regulatory T cells. HHP killed tumor cells thus represent a powerful tool for clinical cancer immunotherapy approaches.

Despite the continuous introduction of new drugs and further improvements of chemotherapy protocols, it is likely that, at some point, chemotherapy will reach its limits, and clinical efficacy will plateau. Moreover, despite the undeniable success in the treatment of some malignancies, in some tumors, particularly in solid tumors, chemotherapy is rarely curative. A combination of treatment modalities has been a standard strategy for cancer treatment, the combination of surgery with chemo- or radiotherapy being a classical example. Effort should be made not only to design modern immunotherapeutic strategies but also to incorporate immunotherapy approaches into current chemotherapy protocols. Chemotherapy and immunotherapy should not be henceforth considered antagonist forms of therapy, and it is conceivable that their rational combination will substantially improve the prognosis of cancer patients.

Preferred cell lines: Acute lymphoblastic leukemia cell lines,(REH, DSMZ, Braunschweig, Germany), ovarian cancer cells (OV90, ATCC, Teddington, UK), prostate cancer cells (LNCap, ATCC, Teddington, UK) were used. All cell lines were cultured in RPMI 1640 medium (Gibco). All media were supplemented with 10% heat-inactivated fetal bovine serum (Lonza), 100 U/ml penicillin and 2 mmol/L L-glutamine.

Isolation of primary tumor cells: Primary ovarian and prostate cancer cells were obtained from patients undergoing surgery. Leukemic blasts from patients with acute lymphoblastic leukemia were obtained from the bone marrow of (ALL) patients by gradient centrifugation on Ficoll gradient.

Apoptosis induction and detection: Tumor cell death was induced by 10 min treatment with high hydrostatic pressure. For comparative tests tumor cell death was induced by UV light exposure. In this case an energy of 7.6 J/cm$^2$ was applied for 10 min. Cell death was assessed by annexin V fluorescein isothiocyanate staining. Briefly, 2×10$^5$ cells per sample were collected, washed in PBS, pelleted, and resuspended in an incubation buffer containing annexin V fluorescein isothiocyanate antibody. The samples were kept in the dark and incubated for 15 min before the addition of another 400 µl of 0.1% propidium iodide incubation buffer and subsequent analysis on an Aria fluorescence-activated cell sorter (BD Bioscience) using FlowJo software.

Flow cytometric analysis of hsp70, hsp90 and CRT (calreticulin) on the cell surface: A total of $10^5$ cells were plated in 12-well plates and treated the following day with the indicated agents or were—as a control—UV-irradiated (7.6 J/cm$^2$) for 6, 12 or 24 h or were treated for 10 min with high hydrostatic pressure at 21 degrees centigrade's. The cells were collected and washed twice with PBS. The cells were incubated for 30 min with primary antibody diluted in cold blocking buffer (2% fetal bovine serum in PBS), followed by washing and incubation with the Alexa 648-conjugated monoclonal secondary antibody in a blocking solution. Each sample was then analyzed by FACScan (BD Bioscience) to identify cell surface hsp70, hsp90 and CRT.

Detection of HMGB1 release: HMGB1 enzyme-linked immunosorbent assay II kits were obtained from SHINO-TEST CORPORATION (Tokyo, Japan). REH cells, OV90 cells, LNCap cells, primary ovarian cells and leukemic blasts ($10^6$) were plated in 1 ml full medium appropriate for the cell type. Supernatants were collected at different time points, dying tumor cells were removed by centrifugation, and the supernatants were isolated and frozen immediately. Quantification of HMGB1 in the supernatants was assessed by enzyme-linked immunosorbent assay according to the manufacturer's instructions.

Fluorescent microscopy: Immunofluorescence: For surface detection of CRT, the cells were placed on ice, washed twice with PBS and fixed in 0.25% paraformaldehyde in PBS for 5 min. The cells were then washed twice in PBS, and a primary antibody diluted in cold blocking buffer was added for 30 min. After two washes in cold PBS, the cells were incubated for 30 min with the appropriate Alexa 648-conjugated secondary antibody. The cells were fixed with 4% paraformaldehyde for 20 min, washed in PBS for 20 min and mounted on slides.

For phagocytosis, the DCs were stained with Vybrant® DiO cell labeling solution (Invitrogen). The tumor cells were stained with Vybrant® DiI cell labeling solution (Invitrogen) and cultured in the presence of anthracyclins, UV light exposure or 10 min treatment with high hydrostatic pressure at 21 degrees centigrade. Immature DCs (day 5) were fed tumor cells at a DC/tumor cell ratio of 5:1. The cells were fixed with 4% paraformaldehyde for 20 min, washed in PBS for 20 min and mounted on slides with ProLong Gold antifade reagent (Invitrogen).

Generation of tumor-loaded DCs and induction of tumor cell death: DCs were generated by culture of purified CD14$^+$ cells isolated from buffy coats in the presence of granulocyte-macrophage colony-stimulating factor (GM-CSF) (Gentaur, Brussels, Belgium) and interleukin-4 (IL-4) (Gentaur, Brussels, Belgium). Tumor cells were killed by 10 min. treatment with high hydrostatic pressure at 21 degrees centigrade, or—as controls—by UV irradiation or by anthracylines. The extent of apoptosis was monitored by annexin V/PI staining. The cells were extensively washed prior to feeding to DCs. Immature DCs (day 5) were fed tumor cells at a DC/tumor cell ratio of 5:1. In some experiments, pulsed DCs were stimulated with 100 ng/ml of lipopolysaccharide (LPS) (Sigma) for 12 h or 25 µg/ml of Poly I:C (obtained from Invivogen).

FACS analysis of DC phenotype after interaction with killed tumor cells: The phenotype of DCs cultured with tumor cells was monitored by flow cytometry. Tumor cells were killed by a selected cytostatic agent or UV irradiation (comparative examples) or 10 min treatment with high hydrostatic pressure at 21 degrees centigrades (according to the present invention) and were cocultured for 24 h with immature DCs. For some experiments, the DCs and tumor cells were dye-labeled before coculture to monitor phagocytosis. Monoclonal antibodies (mAbs) against the following molecules were used: CD80-FITC, CD83-FITC, CD86-PE, CD14-PE (Immunotech, Marseille, France), CD11c-PE, HLA-DR (BD Biosciences, San Jose, Calif.).

The DCs were stained for 30 minutes at 4° C., washed twice in phosphate-buffered saline (PBS) and analyzed using FACS Aria (BD Biosciences) using FlowJo software. The DCs were gated according to the FSC and SSC properties. The appropriate isotype controls were included, and 50000 viable DCs were acquired for each experiment.

Evaluation of IFN-γ producing tumor-specific T cells: Unpulsed or tumor cells-loaded DCs were added to autologous T cells at a ratio of 1:10 on days 0 and 7 of culture. IL-2 (25-50 international units/mL; PeproTech) was added on days 2 and 7 of culture. The cultures were tested for the presence of tumor-specific T cells 7 to 9 days after the last stimulation with DCs. The induction of tumor-reactive, interferon (IFN)-γ-producing T cells of prostate specific antigen (PSA) reactive T cells by tumor-loaded DCs was determined by flow cytometry. The T cells were stained with anti-human CD8/IFN-γ. Frequency of regulatory T lymphocytes in the culture was analyzed by staining with CD4/CD25 and FoxP3. Regulatory T cells were identified by flow cytometry as CD4 positive, CD25 positive and FoxP3 positive.

The invention and the results obtained by the experiments are illustrated by the Figures:

The schematic drawing shows how a pharmaceutical composition of the present invention can be obtained. Tumor cells obtained either from the patient or from cell lines are treated with high pressure whereby the cells become apoptotic.

Dendritic cells are isolated via leukapheresis. Immature dendritic cells and apoptotic tumor cells are combined whereby mature dendritic cells are produced which can be used as vaccine.

FIG. 2

High hydrostatic pressure induces the expression of heat shock proteins on human tumor cells. The summary of a total of 5 experiments is shown. *P value for comparison with irradiated tumor cells, P<0.05. The time dependent expression of the markers HSP70, HSP90 and calreticulin on two tumor cell lines (OV90 and LNCap) caused by different treatments is shown.

FIG. 3

Figure 3:
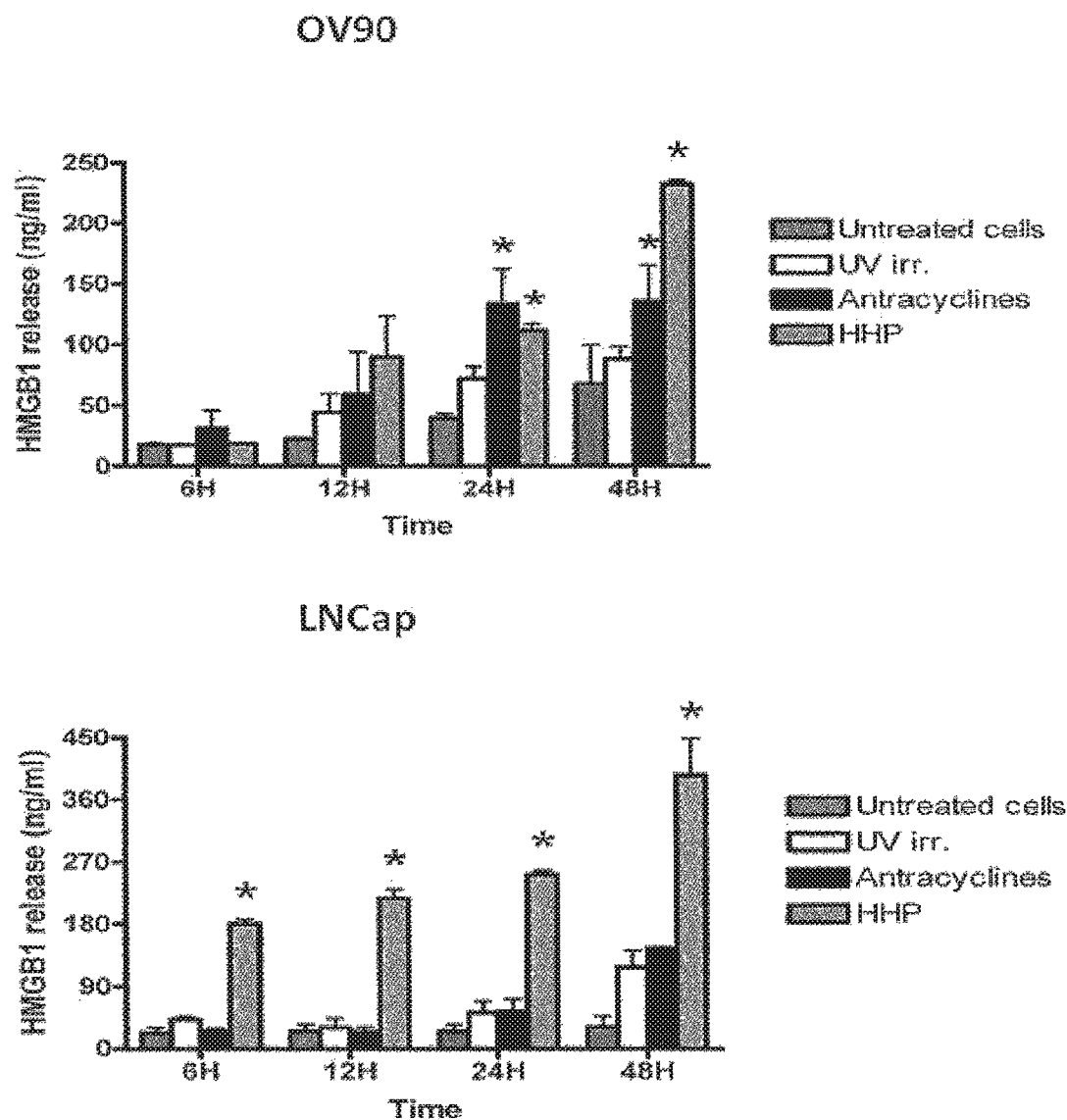

High hydrostatic pressure induces the release of HMGB1 (high-mobility group protein B1) from treated tumor cells (OV90 and LNCap). HMGB1 is a cytokine mediator of inflammation. The summary of a total of 5 experiments is shown. *P value for comparison with irradiated tumor cells, P<0.05. FIG. 3 shows that concerning the time dependent release of HMBG1 the HHP treatment is much more effective than other conventional treatments.

FIG. 4

The kinetics of phagocytosis of high hydrostatic pressure treated tumor cells by immature DCs. Summary of 5 independent experiments and representative results are shown. In the experiment either OV90 or LNCap tumor cells were used. HHP treatment is compared with UV treatment at 0° C. and 37° C.

FIG. 5

The phenotype of dendritic cells based on the markers OD86 and HLA-DR after interaction with high hydrostatic pressure-killed tumor cells (OV90 and LNCap) is shown. Day 5 immature DCs were cultured for 24 h with tumor cells killed by HHP or irradiation. After 24 h, the expression of maturation associated molecules on DCs was analyzed by flow cytometry. LPS was used as control. The mean fluorescence intensity (MFI)are shown. *P value for comparison with irradiated tumor cell-loaded DCs, P<0.05.

FIG. 6

The induction of tumor-specific T cells by dendritic cells loaded with hydrostatic pressure killed tumor cells (LNCap and OV90) is compared with dendritic cells loaded with tumor cells killed by UV irradiation. The data show a summary of five independent experiments. *P value for comparison with irradiated tumor cells, P<0.05.

FIG. 7

Figure 7:
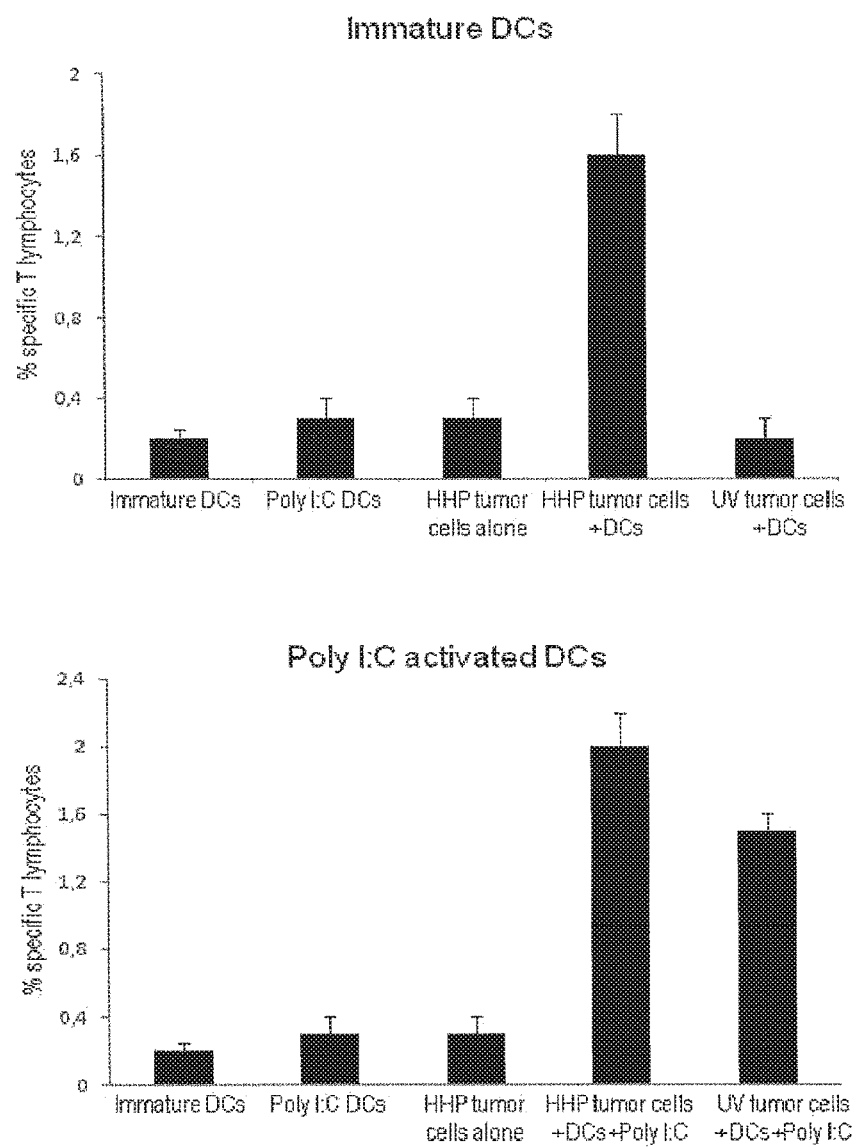

FIG. 7 demonstrates the superiority of the treatment of tumor cells with high hydrostatic pressure (HHP) compared with tumor cells killed by UV irradiation (UV irr). The tests have been performed with prostate cancer cell line (LNCap) and with ovarian cancer cell line (OV90). Controls have been performed with dendritic cells alone and cells stimulated with Poly I:C.

The results summarized in FIG. 7 show the induction of prostate specific antigen (PSA)-specific T cells by dendritic cells loaded with high hydrostatic pressure killed tumor cells (LNCap and OV90, respectively). A comparison was made between high hydrostatic pressure killed tumor cells alone and dendritic cells loaded with tumor cells killed by UV irradiation. The data presented in FIG. 7 show a summary of five independent experiments. * P value for comparison with irradiated tumor cells, P<0.05. FIG. 7 summarizes the results obtained in example 7.

FIG. 8

The induction of regulatory T cells by high hydrostatic pressure killed tumor cells is compared with the induction of Tregs by UV irradiated tumor cells. The data show a summary of five independent experiments.

Figure 8:
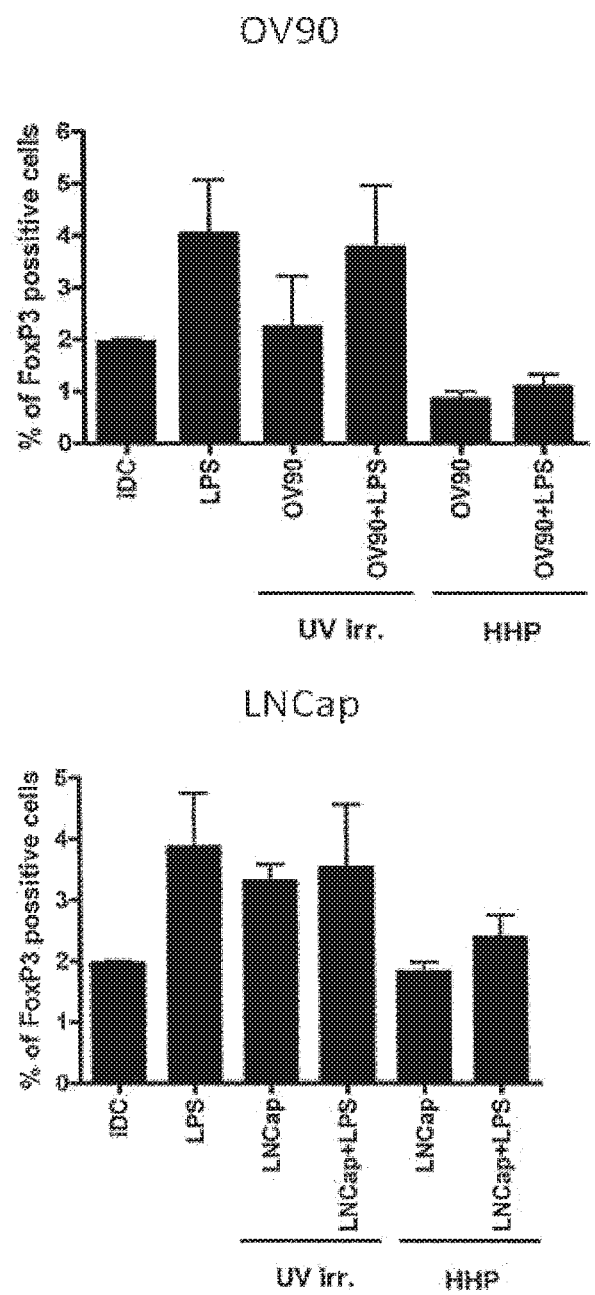

The experiments summarized in FIG. 8 show that the teaching of the present invention can be applied to different types of tumors. The upper part of FIG. 8 shows the experiments performed with ovarian cancer cells (OV90). The lower part shows the experiments performed with prostate cancer cell line (LNCap). In the experiments the concentration of Fox P3 (Forkhead Box P3) has been determined in order to further differentiate the regulatory T cells (Tregs). The experiments show that tumor cells treated according to the invention with HHP do induce lower numbers of regulatory T cells than UV irradiated tumor cells.

FIG. 9

The results of an in vivo study are shown wherein patients were treated with a tumor vaccination as disclosed herein. All patients had radical prostatectomy or radiotherapy. As relevant parameter the PSA doubling time has been determined. According to Antonarakis et al., BJU Int. 2011, 108(3), p. 378-385, the PSA doubling time is the strongest determinant of metastatic free survival time and overall survival time of patients with prostate specific antigen (PSA)-recurrent prostate cancer. PSA doubling time means the time difference wherein the PSA value is doubled. The higher the PSA doubling time is, the better the survival prospect for the treated patient is. By applying the tumor vaccination of the present invention the PSA doubling time could be substantially prolonged.

*P value for comparison with irradiated tumor cells, P<0.05.

FIG. 10

Figure 10:
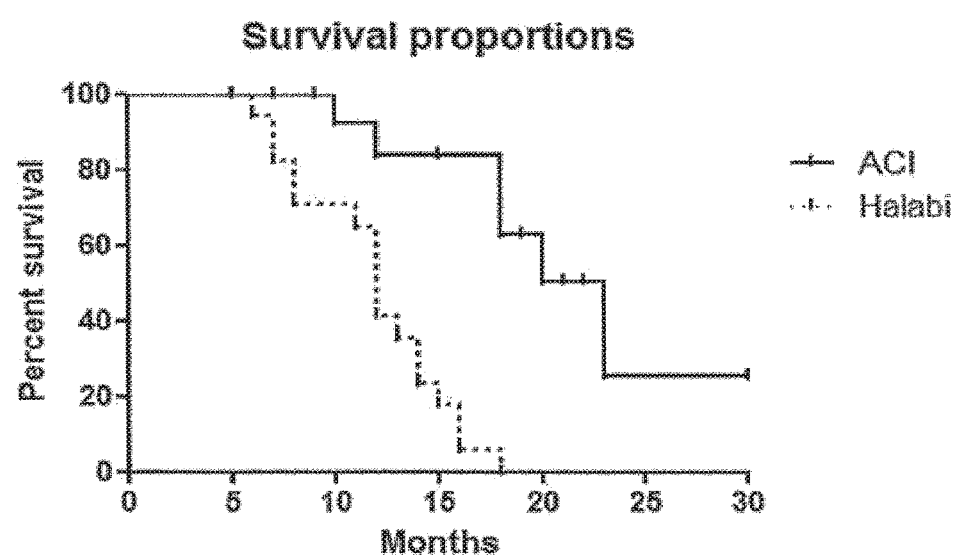

FIG. 10 is a Kaplan-Meier survival curve of patients at a late stage of prostate cancer which were treated according to the present invention.

In the Kaplan-Meier survival curve each death of a patient causes a drop of the percent survival starting from 100% to lower values. The Halabi nomogram is the normally expected reduction of survivors whereby the medium survival time is 12 months.

The active cancer immunotherapy using the cancer vaccine as described herein results in a prolongation of the medium survival time to 23 months.

The present invention is further illustrated by the following examples which are, however, not limiting:

EXAMPLES

Example 1

Figure 1:
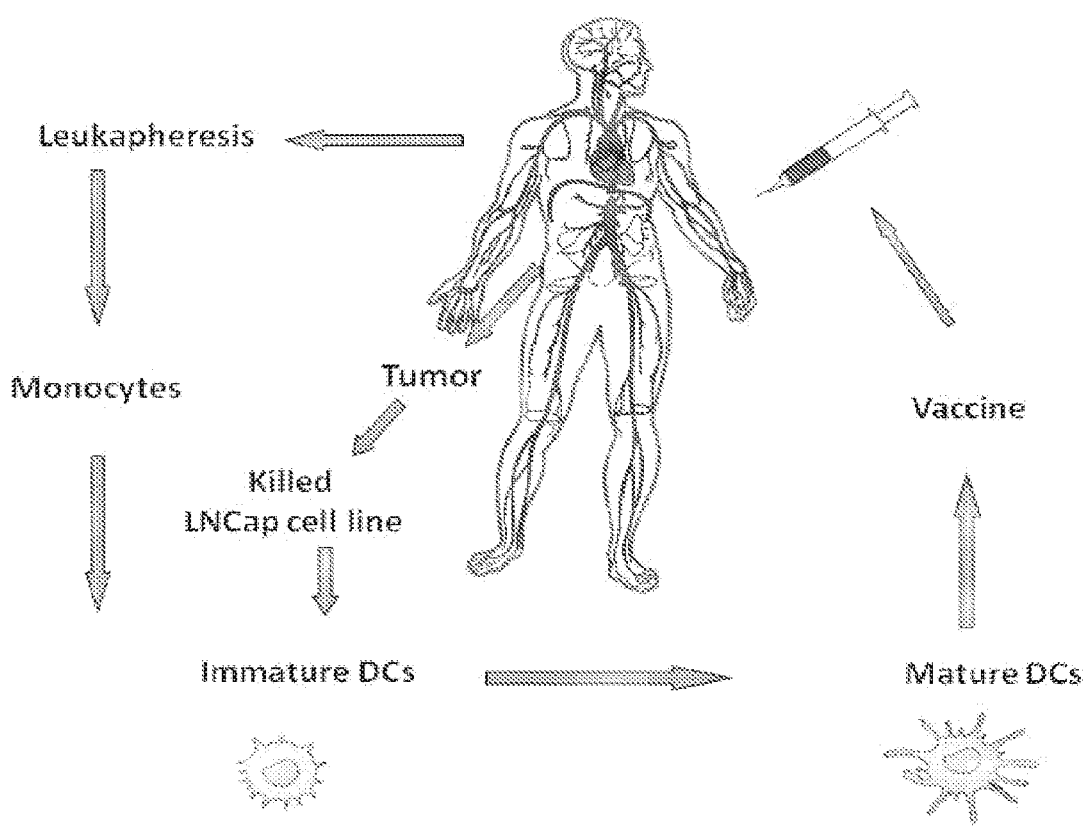
FIG. 1
Figure 2:
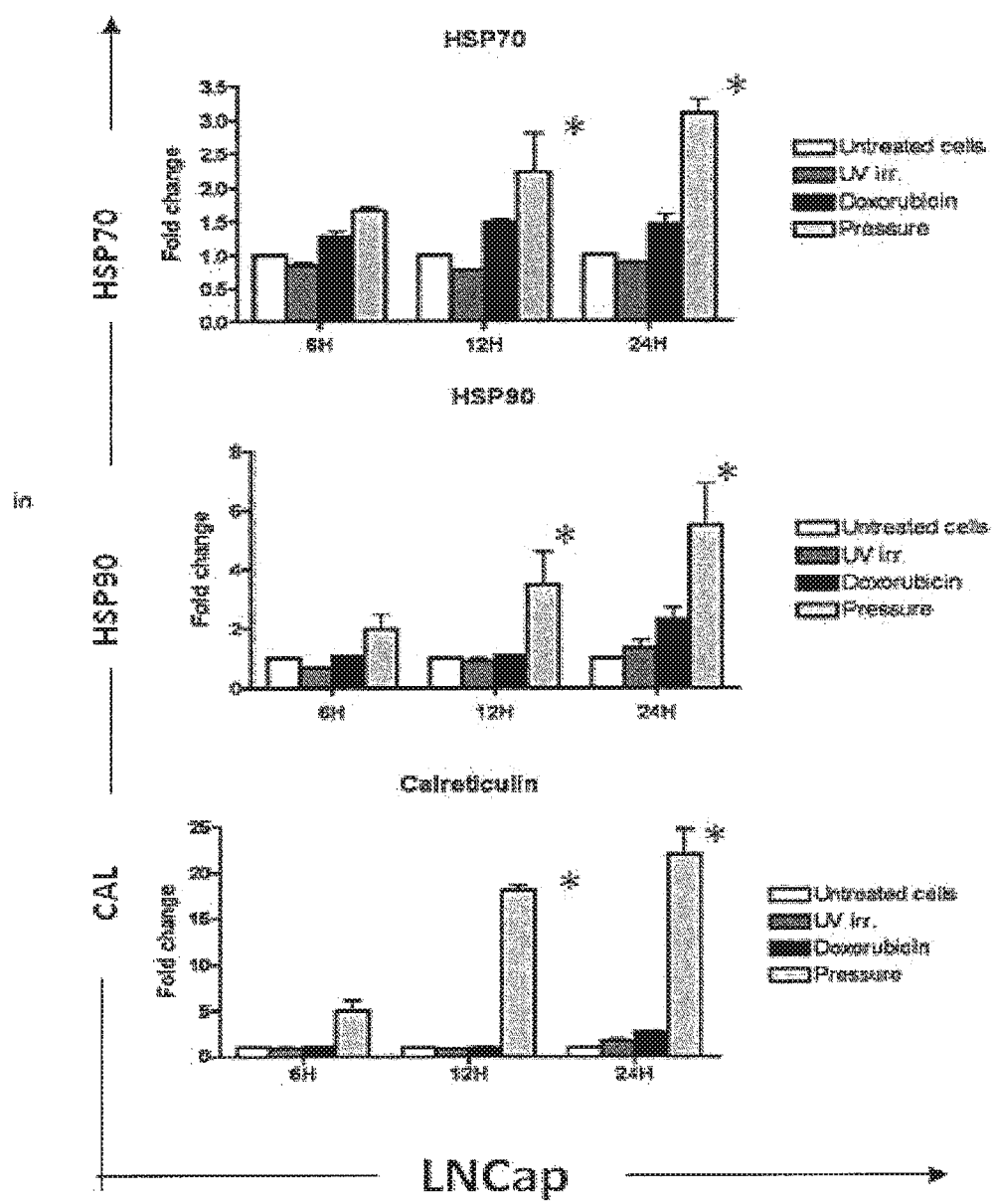
Figure 2:
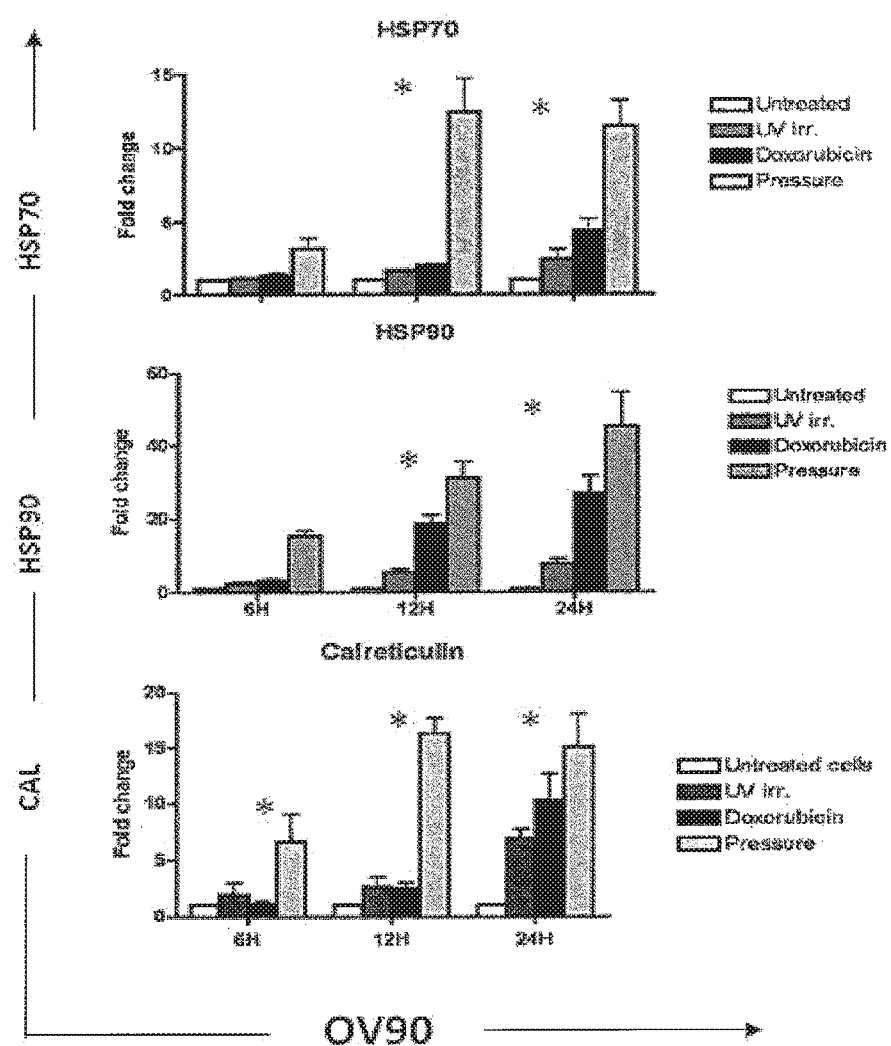

Expression of immunogenic cell death markers hsp70, hsp90 and calreticulin by human cancer cell lines and human primary tumor cells after the treatment with high hydrostatic pressure Leukemic, ovarian and prostate cancer cell lines and primary tumor cells were treated for 10 min with high hydrostatic pressure (HHP, 200 MPa) at 21 degrees centigrade's and the expression of the known immunogenic cell death markers hsp70, hsp90 and calreticulin was monitored at 6, 12 and 24 h. Significant expression of calreticulin, hsp70 and hsp90 was detected 6, 12 and 24 h after HHP treatment for all tested tumor models. The expression of immunogenic molecules was significantly higher than the expression induced by anthracyclins, the only known inducers of immunogenic cell death (FIG. 2). Increased expression of calreticulin and heat shock proteins after HHP treatment was accompanied by their translocation to the cell surface. HHP treatment also induced a rapid and substantial release of HMGB1, a soluble marker of immunogenic cell death. Release of HMGB1 was much higher than in the case of UV irradiation or anthracyclines. (FIG. 3).

Maximal release of HMGB1 nuclear protein was detected 48 h after the induction of tumor cell death.

Example 2

Treatment of Tumor Cells by High Hydrostatic Pressure Increases Their Phagocytosis by Antigen Presenting Cells In view of the established role of calreticulin as an 'eat me' signal, the rate of phagocytosis of tumor cells killed by high hydrostatic pressure by dendritic cells (DCs) was investigated, the most efficient antigen presenting cells that are crucial for the initiation of an immune response. High hydrostatic pressure treated tumor cells were phagocytosed at faster rate and to a higher extent than the tumor cells killed by other modalities, such as anthracyclines or UV irradiation. After 12 h, the extent of phagocytosis of leukemic cells treated with HHP was 4-fold higher than of cells killed by UV irradiation.

Figure 4:
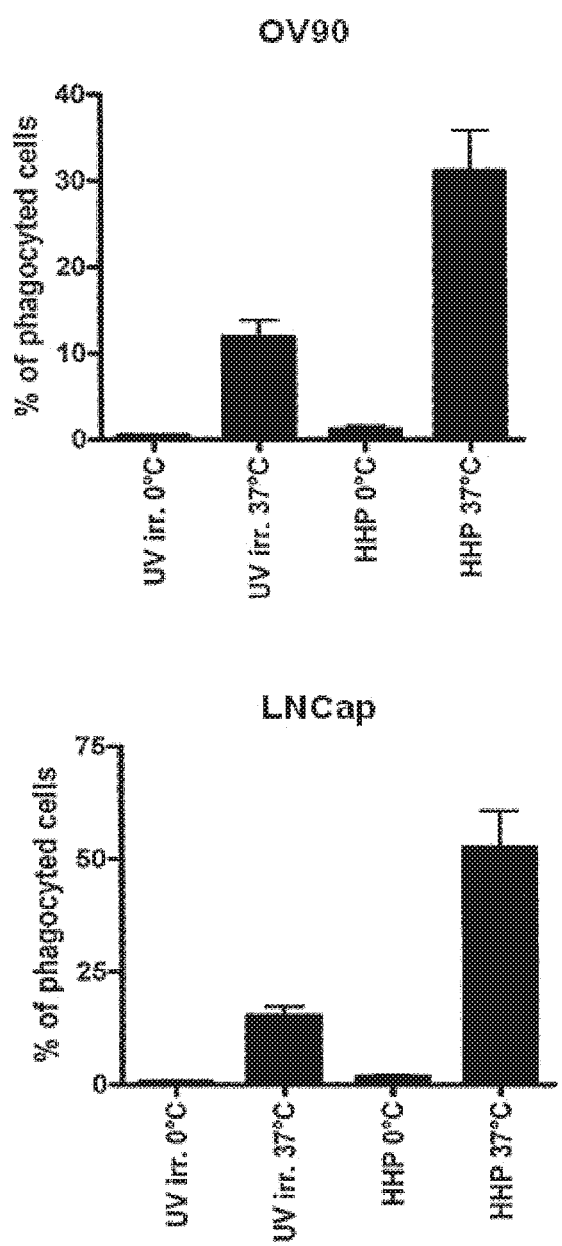

Similarly, the kinetics of phagocytosis of high hydrostatic pressure treated tumor cells by immature DC was investigated. Summary of 5 independent experiments and representative results are shown. In the experiment either OV90 or LNCap tumor cells were used. HHP treatment is compared with UV treatment at 0° C. and 37° C. (FIGS. 4a and 4b).

Example 3

Figure 5:
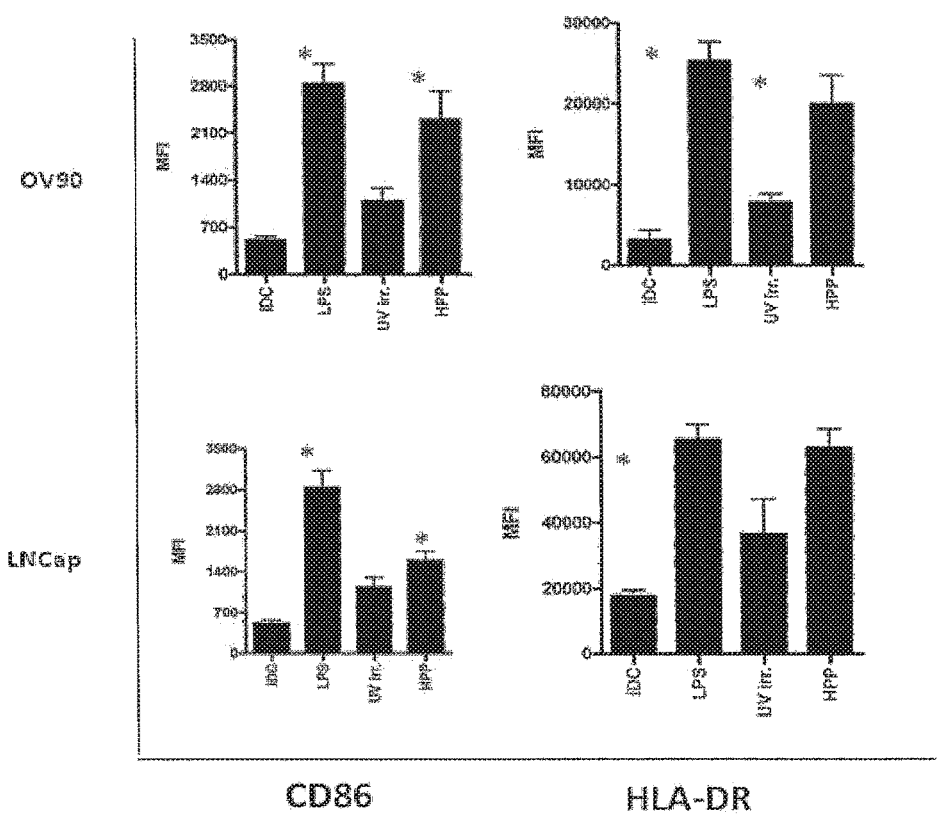
Figure 6:
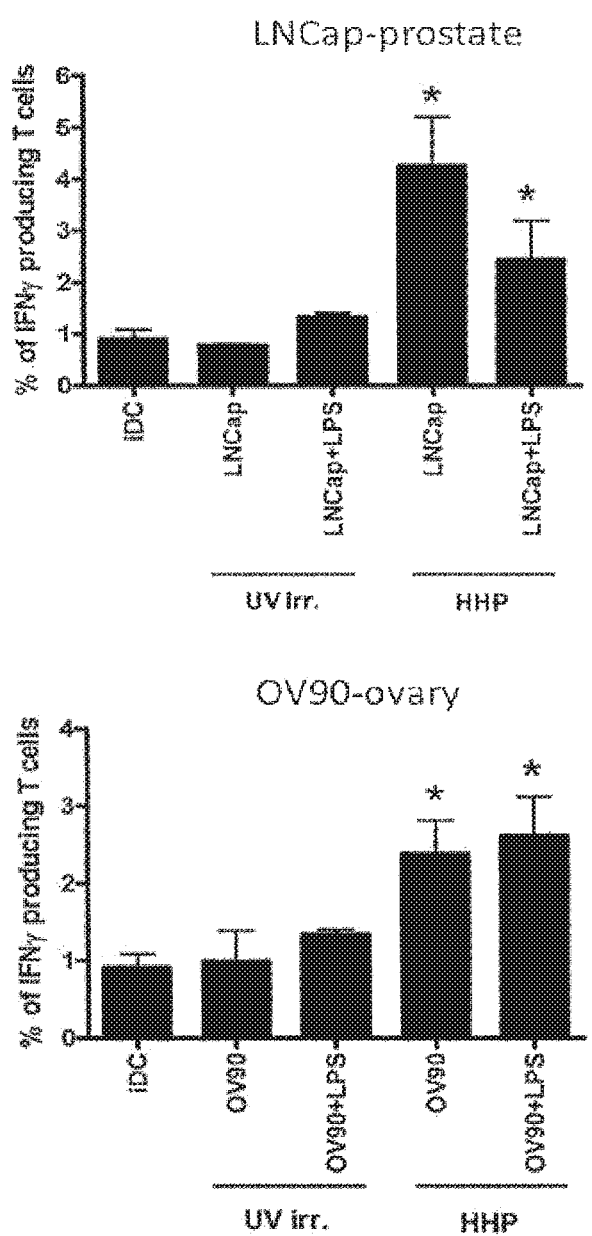

Phagocytosis of High Hydrostatic Pressure-Treated Tumor Cells Induces the Maturation of DCs The ability of DCs to activate the immune response depends on their activation status and the expression of costimulatory molecules. In normal circumstances the most efficient maturation of DCs is induced by molecules derived from pathogens, such as lipopolysacharide (LPS) from Gram negative bacteria. Only activated (mature) DCs that express high levels of costimulatory molecules can initiate the immune response. We analyzed the phenotype of DCs that phagocytosed tumor cells killed by the HHP. The interaction of DCs with HHP-treated tumor cells induced the upregulation of costimulatory molecules (CD86, CD83) and maturation associated molecules (HLA-DR) to a similar extent as activation by LPS (FIG. 5). Thus tumor cells killed by HHP can induce DCs maturation comparable to pathogen derived LPS.

Example 4

DCs Presenting High Hydrostatic Pressure Treated Tumor Cells Induce Tumor-Specific T Cells and Induce Low Numbers of Inhibitory Regulatory T Cells To investigate whether tumor cells treated with HHP and expressing immunogenic cell death markers induce antitumor immunity, we evaluated the ability of tumor cell-loaded DCs to activate tumor cell-specific T cell responses. Tumor cells killed by HHP were cocultured with immature DCs with or without subsequent maturation with LPS. These DCs were then used as stimulators of autologous T cells, and the frequency of IFN-γ-producing T cells was analyzed one week later after restimulation with tumor cell-loaded DCs. DCs pulsed with HHP killed tumor cells induced a greater number of tumor-specific IFN-γ-producing T cells in comparison with DCs pulsed with irradiated cells, even in the absence of additional maturation stimulus (LPS).

Additionally, the frequency of regulatory T cells (Tregs) induced in DC and T cell cocultures was also tested. Induction of Tregs is undesirable in the case of tumor immunotherapy as Tregs inhibit the immune response directed against the tumor. DCs pulsed with tumor cells killed by HHP had a lower capacity to expand regulatory T cells when compared with both immature DCs and LPS-activated DCs (FIG. 8). The FoxP3 surface marker is specific for regulatory T cells.

Example 5

Active cellular immunotherapy can be administered as a single treatment modality in the case of minimal residual disease after primary treatment of the tumor by surgery or radiotherapy. In prostate cancer it may concern patients with signs of biochemical relapse (increasing levels of prostate-specific-antigen PSA in the peripheral blood measured by ultrasensitive method).

The best results of the present invention can be obtained when the primary tumor is removed from the patient by surgery. The pharmaceutical composition as described in the present application can be produced from the tumor cells which have been isolated from the tumor tissue or from tumor cell lines.

A patient (68 years old) suffering from prostate cancer was diagnosed at an early stage of the tumor development. Tumor was removed but few months after the surgery rising levels of PSA were detected. The patient thus underwent leukapheresis and immature dendritic cells were differentiated from isolated monocytes. Tumor cells from the prostate cancer cell line were rendered apoptotic treatment with high hydrostatic pressure as described herein and the apoptotic tumor cells were brought into contact with the immature dendritic cells in order to prepare the vaccine composition.

The pharmaceutical composition was divided into aliquots that were frozen in the liquid nitrogen until use. The first application of the tumor vaccination occurred 4 weeks after the detection of the biochemical relapse of the prostate cancer. Booster applications followed every four weeks for a period of one year.

Vaccination induced an immune response against the small number of surviving tumor cells that has lead to a substantial slowing down of regrowth of tumor cells and resulted in the prolongation of the survival of the patient.

Example 6

In advanced cancer patients, active cellular immunotherapy should be combined with chemotherapy (i.e. docetaxel in prostate cancer) according to the concept of chemoimmunotherapy.

A patient (76 years old) suffering from advanced prostate cancer was treated according to the present invention. The usual chemotherapy was combined with the active cellular immunotherapy as disclosed herein. The patient has been treated at the age of 65 years with prostate tumor. After removal of the tumor by surgery and hormone treatment the level of PSA (prostate specific antigen) was kept at a low level showing that the prostate cancer cells did not grow. After 12 months of hormone therapy metastatic prostate cancer developed at several positions in the body (in particular in the bones) and the tumor became hormone refractory. The patient was approved for the treatment of hormone refractory prostate cancer with docetaxel in combination with active cellular immunotherapy based on dendritic cells.

Before the chemotherapy started, immature dendritic cells were generated from monocytes obtained during leukapheresis. Tumor cells from prostate cancer cell lines were treated with hydrostatic pressure for 30 minutes at a pressure of 210 MPa at 21° C. $10^9$ tumor cells treated according to the present invention were used to pulse $10^9$ immature dendritic cells and aliquots of the mature dendritic cells which have been pulsed before with those tumor cells were deep-frozen in liquid nitrogen and used for later applications.

Active cancer immunotherapy was administered every 4-6 weeks in alternate cycles with standard chemotherapy by docetaxel and alone (after the end of docetaxel treatment) for a period of one year. Combined chemoimmunotherapy led to the stabilization of the disease, decrease in the intensity of bone marrow metastases and longer than expected survival. Patient currently survives for over three years, compared to the expected survival of 6 months at the beginning of the therapy.

Example 7

In Vitro Experiment Showing the Superiority of HHP Killed Tumor Cells Versus UV Killed Tumor Cells In the in vitro experiments the ability of immature dendritic cells, poly I:C activated mature dendritic cells, and dendritic cells loaded with tumor cells which were either HHP treated or UV irradiated was checked with regard to their ability of induce tumor specific immunity. Tumor specific immunity was measured as percent tumor specific T cell lymphocytes.

Dendritic cells with HHP killed tumor cells were directly compared with HHP killed tumor cells alone and dendritic cells loaded with tumor cells killed by UV irradiation. The results of the experiments are shown in FIG. 7.

In order to test the capacity to induce tumor-specific T cells unpulsed or loaded with tumor cells dendritic cells were added to autologous T cells at a ratio of 1:10 on days 0 and 7 of culture. 25-50 international units/mL of IL2 (PeproTech) were added on days 2 and 7 to the culture. The cultures were tested for the presence of tumor specific T cells 7-9 days after the last stimulation with DCs. The induction of tumor-reactive, interferon (IFN)-γ-producing T cells of prostate specific antigen (PSA) reactive T cells by tumor-loaded DCs was determined by flow cytometry. The T cells were stained with anti-human CD8/IFN-γ.

The induction of prostate specific antigen (PSA)-specific T cells by dendritic cells loaded with high hydrostatic pressure killed tumor cells (LNCap) is compared with high hydrostatic pressure killed tumor cells alone and with dendritic cells loaded with tumor cells killed by UV irradiation.

The results of the experiments are shown in FIG. 7. The upper part of FIG. 7 shows that DCs loaded with HHP killed tumor cells can induce tumor specific T cells even in the absence of a maturation signal. DCs loaded with tumor cells killed by UV treatment or HHP killed tumor cells alone do not induce tumor immunity. It is surprising that only HHP treated tumor cells (according to the invention) and immature dendritic cells can induce tumor specific immune response whereas this result cannot be obtained by UV treated tumor cells and immature dendritic cells. Without wishing to be bound to a theory it seems that only the HHP treated tumor cells can together with immature dendritic cells induce the tumor specific T cell immune response. The HHP treated tumor cells seem to act as a kind of activator of the immature dendritic cells whereas UV treated tumor cells do not have this effect.

The lower part of FIG. 7 shows that when Poly I:C treatment is applied the treated HHP tumor cells can better induce specific T cell lymphocytes than tumor cells irradiated with UV.

Example 8

In Vivo Data Obtained With the Tumor Vaccination According to the Present Invention Dendritic cells were obtained from a cohort of patients similar to those as described above. The dendritic cells were pulsed with killed tumor cells as described above and the tumor vaccination was administered repeatedly in up to 12 doses in 4-6 weeks intervals to patients with a biochemical relapse of the prostate cancer after radical prostatectomy or radiotherapy. The progression of the disease in each single patient has been evaluated by the PSA doubling time. Under PSA doubling time the time period is understood which is required for the PSA value to double. PSA doubling time has been shown as the strongest and most reliable determinant of the overall survival and metastatic free survival in men with prostate cancer. Short PSA doubling time correlates with a shortened survival and with shortened time to metastasis appearance (Antonarakis et al., BJU Int., 2012, 108(3); pp 378-385.

Figure 9:
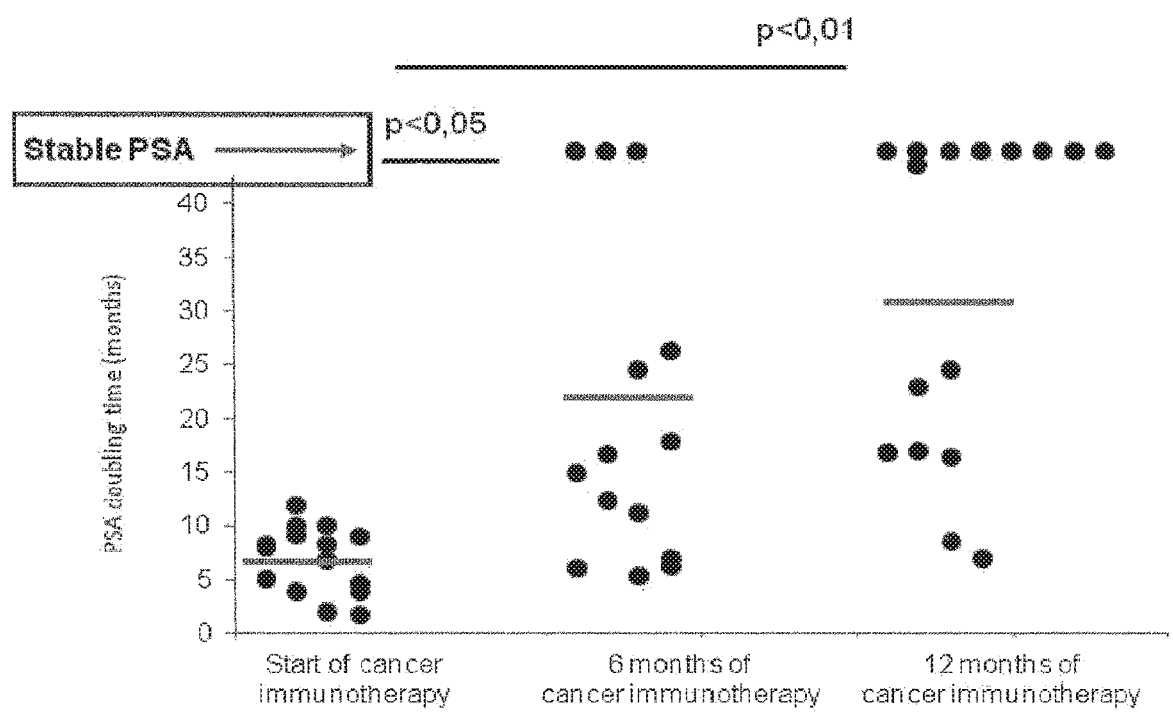

As shown in FIG. 9 the continuous administration of the tumor vaccination according to the present invention in patients with biochemical relapse of the prostate cancer after radical prostatectomy or radiotherapy leads to a significant prolongation of the PSA doubling time. It has been found that by using the tumor vaccination as disclosed herein mean PSA doubling time increases from 5 months before the initiation of cancer immunotherapy to 30 months after 12 months of immunotherapy. This represents a significant benefit to patients with the biochemical relapse of the prostate cancer.

Example 9

Clinical Trial with Patients in Late Stage of Prostate Cancer

In this clinical trial dendritic cells were pulsed with killed tumor cells as described herein. The tumor vaccination was administered repeatedly to patients at a later stage of the prostate cancer. Said patients suffered from castration resistant metastatic prostate cancer. In those patients cancer immunotherapy was administered in alternate dosing schedule with docetaxel chemotherapy.

The survival of the treated cohort was compared to the historical cohort or to the survival estimated by Halabi nomogram. It has been shown that the continuous administration of active cancer immunotherapy significantly prolongs the survival time of treated patients (median survival of 23 months) compared with the cohort of the historical controls based on the expected survival calculated by Halabi nomogram (13 months).

This experiment proves that the tumor vaccination of the present invention substantially extends the survival time of patients which are in a late state of prostate cancer. The average survival expectation of such patients is 13 months without treatment compared to 23 months after treatment with tumor vaccination according to the present invention. This represents a substantial improvement for such patients which are extremely difficult to medicate successfully.

The invention claimed is:

1. A method for producing a mature loaded dendritic cell comprising:
   (i) obtaining monocytes from a patient,
   (ii) culturing the monocytes in the presence of GM-CSF and IL-4 to obtain immature dendritic cells,
   (iii) obtaining tumor cells derived from the patient or from one or more tumor cell lines,
   (iv) inducing apoptosis in the tumor cells by applying high hydrostatic pressure (HHP) of 100 MPa to 300 MPa for 10 min to 2 h,
   (v) loading in vitro the immature dendritic cells obtained in step (ii) with the apoptotic tumor cells obtained in step (iv) to obtain loaded dendritic cells, wherein the immature dendritic cells are combined with the apoptotic tumor cells at a ratio between about 1:1 to about 10:1, and
   (vi) further maturing in vitro the loaded dendritic cells obtained in step (v) by treating the loaded dendritic cells with Poly I:C or LPC to obtain loaded matured dendritic cells.

2. The method of claim 1, wherein the matured loaded dendritic cells have an increase of activation markers CD86 and/or HLA-DR compared to matured dendritic cells loaded with tumor cells killed with UV irradiation.

3. The method of claim 1, wherein the HHP is from 200 MPa to 300 MPa.

4. The method of claim 3, wherein the HHP is applied for 10 to 30 minutes.

5. The method of claim 1, wherein the HHP is applied for 10 minutes to 1 hour.

6. The method of claim 1, wherein the tumor cells are derived from a tumor cell line.

7. The method of claim 1, wherein the tumor cells are derived from a tumor cell obtained from the patient.

8. The method of claim 1, wherein the immature dendritic cell to tumor cell ratio is from 4:1 to 6:1.

9. The method according to claim 1, wherein the tumor cells are prostate cancer cells.

10. The method according to claim 1, wherein the tumor cells are ovarian cancer cells.

11. The method according to claim 1, wherein the mature loaded dendritic cell is formulated for intravenous (IV), intradermal, subcutaneous or intralymphatic administration to apatient.

12. A method for producing a mature loaded dendritic cell comprising:
    (i) obtaining immature dendritic cells from a patient
    (ii) obtaining tumor cells from derived from the patient or from one or more tumor cell lines,
    (iii) inducing apoptosis in the tumor cells by applying high hydrostatic pressure (HHP) of 100 MPa to 300 MPa for 10 min to 2 h,
    (iv) loading in vitro the immature dendritic cells obtained in step (i) with the apoptotic tumor cells obtained in step (iii) to obtain loaded dendritic cells, wherein the immature dendritic cells are combined with the apoptotic tumor cells at a ratio between about 1:1 to about 10:1, and
    (v) further maturing in vitro the loaded dendritic cells by treating the loaded dendritic cells in vitro with Poly I:C or LPS.

13. The method of claim 12, wherein the immature dendritic cells are obtained by leukapheresis.

14. The method of claim 12, wherein the HHP is from 200 MPa to 300 MPa.

15. The method of claim 14, wherein the HHP is applied for 10 to 30 minutes.

16. The method of claim 12, wherein the HHP is applied for 10 minutes to 1 hour.

17. The method of claim 12, wherein the tumor cells are derived from a tumor cell line.

18. The method of claim 12, wherein the tumor cells are derived from a tumor cell obtained from the patient.

19. The method of claim 12, wherein the immature dendritic cell to tumor cell ratio is from 4:1 to 6:1.

20. The method according to claim 12, wherein the tumor cells are prostate cancer cells.

21. The method according to claim 12, wherein the tumor cells are ovarian cancer cells.

22. The method according to claim 12, wherein the mature loaded dendritic cell is formulated for intravenous (IV), intradermal, subcutaneous or intralymphatic administration to apatient.

* * * * *